(12) United States Patent
Natrajan et al.

(10) Patent No.: US 9,512,080 B2
(45) Date of Patent: Dec. 6, 2016

(54) SYNTHESIS OF ACRIDINIUM COMPOUNDS BY N-ALKYLATION OF ACRIDANS

(71) Applicant: Siemens Healthcare Diagnostics Inc., Tarrytown, NY (US)

(72) Inventors: Anand Natrajan, Manchester, NH (US); David Wen, Northborough, MA (US)

(73) Assignee: SIEMENS HEALTHCARE DIAGNOSTICS INC., Tarrytown, NY (US)

( * ) Notice: Subject to any disclaimer, the term of this patent is extended or adjusted under 35 U.S.C. 154(b) by 0 days.

(21) Appl. No.: 14/414,081

(22) PCT Filed: Jul. 10, 2013

(86) PCT No.: PCT/US2013/049910
§ 371 (c)(1),
(2) Date: Jan. 9, 2015

(87) PCT Pub. No.: WO2014/011762
PCT Pub. Date: Jan. 16, 2014

(65) Prior Publication Data
US 2015/0197491 A1    Jul. 16, 2015

Related U.S. Application Data

(60) Provisional application No. 61/670,013, filed on Jul. 10, 2012.

(51) Int. Cl.
C07D 219/04    (2006.01)
(52) U.S. Cl.
CPC ................... C07D 219/04 (2013.01)

(58) Field of Classification Search
CPC .................................................... C07D 219/04
USPC ........................................................... 546/102
See application file for complete search history.

(56) References Cited

U.S. PATENT DOCUMENTS

| | | | |
|---|---|---|---|
| 5,656,426 A | 8/1997 | Law et al. |
| 6,664,043 B2 | 12/2003 | Natrajan et al. |
| 7,781,588 B1 | 8/2010 | Wang et al. |
| 8,034,636 B2 | 10/2011 | Evangelista et al. |
| 8,119,422 B2 | 2/2012 | Natrajan et al. |
| 2008/0248493 A1 | 10/2008 | Mattingly et al. |
| 2010/0256380 A1 | 10/2010 | Natrajan et al. |

FOREIGN PATENT DOCUMENTS

GB            930963 A        7/1963

OTHER PUBLICATIONS

Photochemical behaviour of Acridine in the presence of carboxylic acid. Jacqueline Libman 1976.*
Extended European Search Report dated Oct. 11, 2015.
(Continued)

*Primary Examiner* — Rita Desai
(74) *Attorney, Agent, or Firm* — Kevin Stein (57) ABSTRACT

A method is provided for N-alkylation of acridine compounds by reduction of acridines to corresponding acridans to improve the reactivity of the acridine nitrogen, and subsequent N-alkylation of the acridans in ionic liquid solvents to provide the corresponding acridinium compounds in high yield. This inventive process improves chemical conversion, and does not require the use of highly toxic alkylating agents, such as 1,3-propane sultone.

27 Claims, 3 Drawing Sheets

(56) References Cited

OTHER PUBLICATIONS

Bernthsen, August "Die Acridine" Annalen der Chemie . . . , vol. 224, pp. 1-56, Jan. 1, 1884, Weinheim, Germany.
Bernthsen, August et al. "Ueber die Bildung von Nitrilbasen aus organischen Säuren und Aminen; Synthese der Acridine", Chemische Berichte, vol. 16, No. 2, pp. 1802-1819, Jul. 1, 1883, VCH, Germany.
PCT International Search Report and Written Opinion dated Dec. 3, 2013 (14 Pages).
Natrajan, A. et al. "Facile N-alkylation of acridine esters with 1,3-propane sultone in ionic liquids" Green Chemistry, Feb. 9, 2011, vol. 13, pp. 913-921, entire document.
Fukuzumi. et al. Dehydrogenation versus Oxygenation in Two-Electron and Four-Electron Reduction of Dioxygen by 9-Alkyl-10-methyl-9,10-dihydroacridines Catalyzed by Monomeric Cobalt Porphyrins and Cofacial Dicobalt Porphyrins in the Presence of Perchloric Acid, J. Am. Chem. Soc. 2004, 126, 17059-17066, Published on Web, Nov. 20, 2004.
Shaw, J. E. et al. "Regiospecific Hydrogenation of Quinolines and Indoles in the Heterocyclic Ring" J. Heterocyclic Chem. 24, 1987; pp. 1477-1483.

* cited by examiner

SYNTHESIS OF ACRIDINIUM COMPOUNDS BY N-ALKYLATION OF ACRIDANS

This application claims priority to U.S. Provisional Patent Application No. 61/670,013, filed on Jul. 10, 2012, titled "Synthesis Of Acridinium Compounds By N-Alkylation Of Acridans," the entirety of which is incorporated by reference herein.

FIELD OF INVENTION

The present invention relates generally to synthetic methods for preparing N-alkyl derivatives of heteroaromatic compounds. More particularly, the invention relates to a process for synthesis of acridinium compounds by reduction of acridines to corresponding acridans to improve the reactivity of the acridine nitrogen, and subsequent N-alkylation of the acridans in ionic liquid solvents.

BACKGROUND OF THE INVENTION

Chemiluminescent acridinium compounds have emerged to be extremely useful labels for immunoassays and nucleic acid assays. Hydrophilic acridinium esters containing N-sulfopropyl groups (NSP) are useful for protein labeling as well as for the preparation of small molecule conjugates, as described by Law et al. in U.S. Pat. No. 5,656,426 and Natrajan et al. in U.S. Pat. No. 6,664,043, the disclosures of which are hereby incorporated by reference. Furthermore, acridinium ester labels containing NSP groups display improved aqueous solubility compared to the corresponding N-methyl analogs. These hydrophilic acridinium esters offer improved performance in immunoassays. For example, chemiluminescent acridininum dimethylphenyl esters containing NSP groups have been used as labels in automated immunoassays in Siemens Healthcare Diagnostics' ADVIA: Centaur® systems. These labels exhibit excellent chemiluminescent stability compared to unsubstituted acridinium phenyl esters (Law et al, *J. Biolumin. Chemilumin.*, 1989, 4, 88-98). Improvements to the specific binding of these chemiluminescent labels to an analyte have also been made by incorporating poly(ethylene)glycol (PEG) or zwitterions in the acridinium ester structure (Natrajan et al, *Org. Biomol. Chem.*, 2011, 9, 5092-5103; Natrajan et al, *Anal. Biochem.*, 2010, 406, 204-213).

The synthesis of acridinium esters containing N-sulfopropyl groups entails N-alkylation of the corresponding acridine esters with the potent carcinogen 1,3-propane sultone. In general, this reaction is carried out by heating the acridine ester with a vast excess of propane sultone in the absence of solvent, as described by Law et al in U.S. Pat. No. 5,656,426, incorporated by reference herein. These harsh conditions for the N-alkylation reaction are necessitated by the poor reactivity of the hindered acridine nitrogen towards alkylating reagents.

A major disadvantage of this reaction is that 1,3-propane sultone is quite toxic and poses a significant health hazard (Bolt and Golka, *Toxicol. Lett.*, 2004, 151, 251-254; Ulland et al, *Nature*, 1971, 230, 460-461). As reported recently by Bolt and Golka in *Toxicology Lett.* 2004, 151, 251-254, the disclosure of which is incorporated by reference, propane sultone is directly alkylating, genotoxic and carcinogenic. Bolt and Golka observe that "malignancies observed within a group of persons exposed to 1,3-propane sultone appear surprisingly consistent with the expectations from the available animal studies" and are characterized by latency times up to 30-40 years or more after limited periods of past exposure. Thus, chemical transformations under reaction conditions that limit the use this toxic reagent are desirable.

More recently, Natrajan and Wen, in *Green Chem.*, 2011, 13, 913-921 and U.S. Patent Application Publication No. 2010/0256380 described a synthetic protocol for the N-alkylation of acridine esters in ionic liquids. The increased reactivity of the acridine ester precursors with 1,3-propane sultone in ionic liquids provide for the synthesis of a variety of functionalized acridinium esters containing N-sulfopropyl groups with reduced side reactions or decomposition. Although this synthetic protocol in ionic liquids reduced the amount of 1,3-propane sultone necessary for N-alkylation of the acridine compound, sultones, particularly the highly toxic 1,3-propane sultone, remained a necessary part of the reaction.

The above cited literature points to the general difficulty in introducing the N-sulfopropyl group in acridine compounds which necessitates conducting the reaction using highly reactive alkylating reagents. It is important to eliminate the use of the carcinogenic reagent 1,3-propane sultone altogether in the synthesis of acridinium esters with N-sulfopropyl groups. It is therefore an object of the invention to provide a synthetic process for N-alkylating an acridine compound using a suitable and relatively benign alkylating agent to achieve this chemical transformation in good yields.

SUMMARY OF THE INVENTION

In accordance with a first aspect of the invention, a method is provided for N-alkylation of an acridine compound, the method comprising reacting an acridine compound with a reducing agent to thereby convert the acridine compound to an acridan compound, subsequently reacting the acridan compound with an alkylating agent in an ionic liquid solvent to thereby convert the acridan compound to an N-alkylacridan, and oxidizing the N-alkylacridan to thereby convert said N-alkylacridan to an N-alkyl acridinium compound. There is essentially no constraint on the structure of the acridine compound, which may comprise acridine ester or sulfonamides.

The preferred alkylating agent according to the foregoing method is a sulfonate, preferably having the structure:

where n is an integer from 1 to 20, preferably from 1 to 10, more preferably from 1 to 5, L' is a halogen or —OR$^L$, wherein R$^L$ is an acetyl or a sulfonyl group, optionally substituted with one or more linear, branched or cyclic alkyl groups, wherein said alkyl groups optionally comprise one or more heteroatoms and optionally include one or more unsaturated bonds, and A is a counterion, preferably a sodium or potassium cation.

In some embodiments, L' is chloride, bromide, or —OR$^L$, where R$^L$ is selected from the group consisting of acetyl, methanesulfonyl, or p-toluenesulfonyl groups.

A preferred alkylating agent is sodium 3-bromopropanesulfonate.

The reducing agent is not particularly restricted and can, for example, be a metal hydride or a borane. In one embodiment, the reducing agent is a borane complex of an amine or a cyanoborohydride complex comprising an alkali metal cation. Preferably, the reducing agent is selected from the group consisting of sodium borohydride, lithium borohydride, potassium borohydride, sodium cyanoborohydride or potassium cyanoborohydride or picoline-borane. More preferably, the reducing agent is sodium cyanoborohydride or picoline-borane. In another embodiment, the reducing agent is a metal catalyst, preferably comprising platinum or palladium.

Preferred ionic liquid solvents according to the foregoing method have the form:

where n is an integer from one to nine; and

Y is selected from the group consisting of tetrachloroaluminate; hexafluroantimonate; dicyanamide; thiocyanate; nitrate; chloride; iodide; trifluoroacetate; tetrafluoroborate; hexafluorophosphate; methylsulfonate; trifluoromethylsulfonate; tris(pentafluoroethyl)trifluorophosphate; bis(trifluoromethylsulfonyl)imide;

and combinations thereof.

More preferably, the ionic liquid solve comprises [BMIM][PF$_6$] (1-butyl-3-methylimidazolium hexafluorophosphate), [BMIM][BF$_4$] (1-butyl-3-methylimidazolium tetrafluoroborate), or a combination thereof.

The N-alkylation of an acridan compound according to the present invention is preferably conducted in the presence of a base that is unreactive with the alkylating agent under the reaction conditions. Preferably, the base is potassium carbonate, sodium carbonate, or cesium carbonate. In another embodiment, the base is a sterically hindered pyridine derivative, preferably 2,6-di-t-butylpyridine (DtBP) or 2,6-di-t-butyl-4-methylpyridine (DtBMP), or a combination thereof.

In another aspect of the invention, the foregoing method has been found especially useful for preparing acridinium ester compounds having the structure of formula (V):

wherein $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; $R_{10}$ and $R_{11}$ can be the same or different and represent hydrogen, an alkyl, alkenyl, alkynyl, aryl, or aralkyl group containing up to 20 heteroatoms; and wherein $R_{12}$ is —OR. Preferably, $R_{12}$ is —OR, where R is methyl, ethyl, propyl, or isopropyl.

The method according to this aspect comprises:

(a) reacting an acridine compound having the structure of formula (Vb)

wherein $R_7$, $R_8$, $R_{10}$, $R_{11}$ and $R_{12}$ are as defined above, with a reducing agent to thereby convert said acridine compound to an acridan compound having the structure of formula (Vd):

wherein $R_7$, $R_8$, $R_{10}$, $R_{11}$ and $R_{12}$ are as defined above;

(b) reacting said acridan compound with an alkylating agent in an ionic liquid solvent to thereby convert said acridan compound to an N-alkylacridan having the structure of formula (Ve):

wherein $R_7$, $R_8$, $R_{10}$, $R_{11}$ and $R_{12}$ are as defined above; and (c) oxidizing said N-alkylacridan to thereby convert said N-alkylacridan to said acridinium ester.

In a further aspect, a method is provided for preparing an acridinium ester compound having the structure of formula (VI):

(VI)

wherein $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; and wherein $R_{13}$ and $R_{14}$ can be the same or different and represent an alkyl, alkenyl, alkynyl, aryl, or aralkyl group containing up to 20 heteroatoms.

The method according to this aspect comprises:
(a) reacting an acridine compound having the structure of formula (VIa)

(VIa)

wherein $R_7$, $R_8$, $R_{13}$ and $R_{14}$ are as defined above, with a reducing agent to thereby convert said acridine compound to an acridan compound having the structure of formula (VIb):

(VIb)

wherein $R_7$, $R_8$, $R_{13}$ and $R_{14}$ are as defined above;
(b) reacting said acridan compound with an alkylating agent in an ionic liquid solvent to thereby convert said acridan compound to an N-alkylacridan having the structure of formula (VIc):

(VIc)

wherein $R_7$, $R_8$, $R_{13}$ and $R_{14}$ are as defined above; and
(c) oxidizing said N-alkylacridan to thereby convert said N-alkylacridan to said acridinium ester.

These and other aspects of the invention will be better understood by reference to the following detailed description, accompanying figures, and appended claims.

DETAILED DESCRIPTION

All terms used herein are intended to have their ordinary meaning in the art unless otherwise specified. The term "ionic liquid" refers to a room temperature or near room temperature (e.g., ±20° C.) ionic liquid (or molten salt) which is a material containing only ionic species without any neutral molecules and having a melting point of less than 298 K. By the phrase "without any neutral molecules" is meant that the ionic liquid consists of a cationic and anionic component at its most fundamental level, but is not intended to mean that the solvent system which comprises the ionic liquid solvent does not comprise neutral species in addition to the ionic liquid.

The present invention is directed generally to a process for the synthesis of acridinium compounds, in particular acridinium esters and acridinium sulfonamides formed at the C-9 position of the acridinium nucleus, by conversion of the corresponding acridine compounds to acridan compounds, subsequent N-alkylation in ionic liquids (ILs) of the acridan compounds, and oxidation of the N-alkylated acridan compounds to the desired acridinium compounds. Conversion of an acridine compound to a corresponding acridan compound improves the reactivity of the acridine nitrogen and is contemplated to be useful in general for synthesis of acridinum compounds having various functional groups attached to the acridinium nitrogen.

The process of the present invention provides for an environmentally clean process with excellent conversion. It is believed that the improved reactivity of the acridine nitrogen, by first converting the acridine to a corresponding acridan, allows for the use of less reactive reagents, which are typically less toxic, in attaching various functional groups to the acridinium nitrogen. This process not only offers an opportunity to curtail the use of the carcinogen propane sultone, but the improved reactivity of the acridine nitrogen provides an improved rate of conversion and offers a protocol that is suitable for commercial scale-up synthesis of a variety of acridinium compounds.

The inventive transformation may be illustrated generally as follows:

wherein acridine compound 1 is converted to acridan compound 2 by treatment with a reducing agent. The acridan compound 2 is then converted to N-alkyl acridan compounds 3 by treatment with an alkyating reagent $LR^AX$ in an ionic liquid solvent, preferably in the presence of a base. The N-alkyl acridan compound 3 is subsequently converted to N-alkyl acridinium compounds 4 by oxidation. The alkylating reagent $LR^AX$ comprises an alkyl portion $R^A$, a leaving group L, and X may be any suitable functional group. Furthermore, the alkylating agent may be an ionic complex further comprising a suitable cation (not shown). $R^A$ may be a divalent radical and that X may be advantageously included in the acridinium compound 4 to impart functionality (e.g., increased hydrophilicity or as a starting point for further transformations) or a functional group for further chemical transformations. While this scheme illustrates the simple case of an unsubstituted acridine compound, the advantages of the invention may be most fully realized where the acridine compound bears addition functional groups, such as ester or sulfonamide groups at the C-9 position and/or electron donating groups at the C2 and/or C7 positions of the acridine nucleus.

Advantages of the inventive process include improved chemical conversion, and does not require the use of highly toxic alkylating agents, such as sultones, including the potent carcinogen 1,3-propane sultone. The present process also offers a general procedure for the high yield synthesis of hydrophilic acridinium esters containing N-sulfoalkyl groups, such N-sulfopropyl groups, on at least a gram scale, and may be suitable for synthesis on a commercial scale. The difference in reactivity between the acridine nitrogen and the corresponding acridan nitrogen towards an alkylating agent in ionic liquids is illustrated below in Examples 1 and 2.

The reducing agent may be any suitable compound for hydrogenating an acridine to an acridan. Typically, the reducing agent is a metal hydride or a borane complex of an amine. More typically, the reducing agent is a boron hydride or a boron and nitrogen hydride, or a borane-heterocyclic amine complex. The boron hydride or the boron and nitrogen hydride may optionally be substituted with a cyano group. More typically, the reducing agent is a borane complex or a cyanoborohydride complex comprising an alkali metal cation. Preferably, the reducing agent is selected from the group consisting of sodium borohydride, lithium borohydride, potassium borohydride, sodium cyanoborohydride or potassium cyanoborohydride or picoline-borane.

In another embodiment, the reducing agent may be any suitable catalyst for catalytic hydrogenation of the acridine nitrogen. The catalyst may be a homogenous or a heterogenous catalyst. For example, the reducing agent may be a metal catalyst, such as platinum, palladium, rhodium, or ruthenium. Typically, the metal catalyst is platinum or palladium. Preferably, the catalyst is a heterogenous catalyst of metal on carbon. More preferably, the catalyst is either palladium on carbon or platinum on carbon.

The alkylating agent may be any organic moiety comprising a leaving group, such as sulfonates, esters of haloacetic acid (e.g., methyl bromoacetate), and compounds of the formula $R^AX'$ where $R^A$ is any suitable $C_{1-20}$ hydrocarbon radical, such as an alkyl, preferably a $C_{1-6}$ alkyl, optionally substituted with one or more heteroatoms, typically one to six heteroatoms, such as oxygen, nitrogen and/or sulfur, and optionally including unsaturated bonds, and X' is any leaving group such as halogen (preferably iodo) or triflate. Preferably, the alkylating agent excludes highly toxic reagents, such as sultones. The sulfonates will have the general structure:

(I)

where n is an integer from 1 to 20, typically from 1 to 10, more typically from 1-5, and preferably is 3.

L' can be any suitable leaving group, typically, L' is a halogen or —$OR^L$, where $R^L$ is an acetyl or a sulfonyl group, optionally substituted with one or more $C_{1-20}$ hydrocarbon radicals, such as an alkyl, such as a $C_{1-10}$ or $C_{1-6}$ alkyl, wherein the hydrocarbon radicals may be linear, branched or cyclic and are each independently optionally substituted with one or more heteroatoms, preferably one to six heteroatoms, such as oxygen, nitrogen and/or sulfur, and optionally including unsaturated bonds. More typically, L' is chloride, bromide, or $OR^L$, where $R^L$ is selected from the group consisting of acetyl, methanesulfonyl, or p-toluenesulfonyl groups.

A can be any suitable counterion, such as a cation, typically A is an alkali metal cation, more typically, A is a sodium or a potassium cation.

In some embodiments, the alkylating agent is less reactive than 1,3-propane sultone. Preferably, the alkylating agent is sodium 3-bromopropanesulfonate.

After the acridine compound 1 is reduced to an acridan compound 2, the acridan compound 2 is reacted in a mixture comprising an ionic liquid. The ionic liquid is liquid at or near room temperature. Ionic liquids typically comprise an organic cation and an anion, the anion sometimes but not always, being a purely inorganic species. The organic cation is typically a quaternary ammonium compound, including tetra-alkyl ammonium, and more typically is an N-alkyl heteroaromatic species, for example N-alkylpyridinium, 1,3-dialkylimidazolium, N-dialkylpyrrolidinium, or the like. In addition, phosphonium and sulphonium-based ionic liquids may also be suitable, although these are less preferred cations according to the invention.

Of the various N-alkyl heteroaromatic cations, special mention may be made of N-alkylpyridinium and 1,3-dialkylimidazolium cations. N-alkylpyridinium cations may generally be represented by formula (II):

(II)

where $R_1$ is a $C_{1-20}$ hydrocarbon radical, such as alkyl, alkenyl, alkynyl, aryl, and aralkyl (e.g., benzyl), each optionally including one or more heteroatoms selected from halogen, oxygen, sulfur, and combinations thereof, with the proviso that the heteroatoms do not form moieties reactive with the alkylating reagent or with the acridine compound; and where R' is intended to represent optional substitution at one or more carbon atoms of the ring, and will typically be selected from hydrogen, halogen, or alkyl (methyl, ethyl, propyl, butyl, pentyl, hexyl, etc.), and which also may comprise one or more heteroatoms, subject to the same proviso as above. Often $R_1$ will be a $C_{1-20}$ alkyl group, more typically a $C_{1-10}$ alkyl group, preferably a $C_{1-6}$ alkyl group, with methyl, ethyl, propyl, isopropyl, n-butyl, isobutyl, n-pentyl, neopentyl, and isopentyl being illustrative. R' represents a substituent at any carbon atom and is usually hydrogen, but may also be methyl, ethyl, propyl, and the like. Representative of the various N-alkylpyridinium cations of formula (I) are N-methylpyridinium, N-ethylpyridinium, N-propylpyridinium, N-butylpyridinium, N-pentylpyridinium, and N-hexylpyridinium, without limitation.

In a preferred embodiment, the ionic liquid will comprise a 1,3-dialkylimidazolium cation. Such cations will typically have the structure shown in formula (III):

(III)

where $R_2$ and $R_3$ independently represent $C_{1-20}$ hydrocarbon radicals, such as alkyl, alkenyl, alkynyl, aryl, and aralkyl (e.g., benzyl), each optionally including one or more heteroatoms selected from halogen, oxygen, sulfur, and combinations thereof, with the proviso that the heteroatoms do not form moieties reactive with the alkylating reagent or with the acridine compound; and $R_4$, $R_5$, and $R_6$ are independently selected from hydrogen, halo, alkyl, (methyl, ethyl, propyl, butyl, pentyl, hexyl, etc.), and which also may comprise one or more heteroatoms, subject to the same proviso as above. In preferred embodiments, $R_2$ and $R_3$ will independently be $C_{1-20}$ alkyl groups, more typically $C_{1-10}$ alkyl groups, preferably $C_{1-6}$ alkyl groups, with methyl, ethyl, propyl, isopropyl, n-butyl, isobutyl, n-pentyl, neopentyl, and isopentyl being illustrative. Radicals which include one or more heteroatoms, not reactive under the conditions of the invention, may be exemplified by, for example, alkyl groups having oxa (i.e., ethers) substitution, and fluroalkyl or perfluoroalkyl substituents.

Representative 1,3-dialkylimidazolium cations of formula (II) include, but are not limited to, those given in Table 1.

TABLE 1

Exemplary 1,3-dialkylimidazolium cations of formula (II)

| $R_2$ | $R_3$ | $R_4$ | $R_5$ | $R_6$ |
|---|---|---|---|---|
| CH₃ | CH₃ | H | H | H |
| CH₃ | CH₃CH₂ | H | H | H |
| CH₃ | CH₃CH₂ | CH₃ | H | H |
| CH₃ | CH₃CH₂ | H | CH₃ | H |
| CH₃ | CH₃CH₂ | H | H | CH₃ |
| CH₃ | CF₃CH₂ | H | H | H |
| CH₃ | CH₃CH₂CH₂ | H | H | H |
| CH₃ | CH₃CH₂CH₂ | CH₃ | H | H |
| CH₃ | CH₃CH₂CH₂ | H | CH₃ | H |
| CH₃ | CH₃CH₂CH₂ | H | H | CH₃ |
| CH₃ | CH₃OCH₂CH₂ | H | H | H |
| CH₃ | CH₃CH₂CH₂CH₂ | H | H | H |
| CH₃ | CH₃CH₂CH₂CH₂ | CH₃ | H | H |
| CH₃ | CH₃CH₂CH₂CH₂ | H | CH₃ | H |
| CH₃ | CH₃CH₂CH₂CH₂ | H | H | CH₃ |
| CH₃ | (CH₃)₂CH₂CH₂ | H | H | H |
| CH₃ | CH₃CH₂CH₂CH₂CH₂ | H | H | H |
| CH₃ | CH₃CH₂CH₂CH₂CH₂CH₂ | H | H | H |
| CH₃ | (C₆H₅)CH₂ | H | H | H |
| CH₃CH₂ | CH₃CH₂ | H | H | H |
| CH₃CH₂ | CH₃CH₂ | CH₃ | H | H |
| CH₃CH₂ | CH₃CH₂CH₂ | H | H | H |
| CH₃CH₂ | CH₃CH₂CH₂CH₂ | H | H | H |
| (C₆H₅)CH₂ | CH₃CH₂CH₂ | CH₃ | H | H |
| (C₆H₅)CH₂ | CH₃CH₂CH₂CH₂ | CH₃ | H | H |
| (C₆H₅)CH₂ | (CH₃CH₂)(CH₃)CH | CH₃ | H | H |
| (C₆H₅)CH₂ | CH₃CH₂CH₂CH₂ | CH₃ | H | H |

Special mention may be made of 1-ethyl-3-methyl imidazolium, 1-propyl-3-methyl imidazolium, 1-butyl-3-methyl imidazolium, 1-pentyl-3-methyl imidazolium, 1-hexyl-3-methyl imidazolium, 1-heptyl-3-methyl imidazolium cation, and 1-octyl-3-methyl imidazolium. The 1-butyl-3-methyl imidazolium, which is frequently designated [BMIM] in the literature, is the currently preferred cation in the ionic liquids useful in the practice of the invention.

Other cations contemplated to be suitable include, without limitation, pyrrolidinium cations, such as 1-butyl-1-methylpyrrolidinium, alkyl ammonium cations, including tri(ethyl) hexylammonium and ethyl dimethyl propyl ammonium, and phosphonium cations, for example, tri(hexyl)tetradecylphosphonium.

A wide variety of anions, which may be inorganic or organic species, may be employed as the counterion in the ionic liquid, including without limitation metal or metalloid halide anions, such as tetrachloroaluminate (AlCl₄), tetrabromoaluminate (AlBr₄⁻), hexafluoroantimonate (SbF₆⁻), hexafluoroarsenate (AsF$_6^-$), to name a few. Other suitable anions include, without limitation, halide ions (Cl$^-$, Br$^-$, and I$^-$), perchlorate, hydroxide, F(HF)$_n^-$, tetrafluoroborate (BF$_4^-$), tetrachloroborate, hexafluorophosphate (PF$_6^-$), nitrate, trifluoromethane sulfonate (triflate), methylsulfonate (mesylate), p-toluenesulfonate (tosylate), dicyanamide, perfluorobutyl sulfonate, trifluoroacetate (CF$_3$COO$^-$), CF$_3$CF$_2$CF$_2$COO$^-$, dibutyl phosphate, carbonate, lactate, tris(pentafluoroethyl)trifluorophosphate [(C$_2$F$_5$)$_3$PF$_3$]$^-$, bis(trifluoromethylsulfonyl)imide [(CF$_3$SO$_2$)$_2$N$^-$], bis(perfluoroethylsulfonyl)imide, hydrogen sulfate, methyl carbonate, C$_{1-16}$ alkyl sulfate, including for example, methyl sulfate, ethyl sulfate, and octyl sulfate, 2-(2-methoxyethoxy)ethyl sulfate, thiocyanate, tris(trifluoromethylsulfonyl)methide [(CF$_3$SO$_2$)$_3$C$^-$], and the like.

In one embodiment, the anion is a fluorine-containing anion. In another embodiment, the anion is an inorganic fluorine-containing ion. Preferably, the anion is tetrafluoroborate (BF$_4^-$) or hexafluorophosphate (PF$_6^-$). While any ionic liquid which is molten at room temperature is contemplated to be useful according to the invention, the preferred ionic liquids will be tetrafluoroborate (BF$_4^-$) or hexafluorophosphate (PF$_6^-$) salts of the cations according to formulas (II) and (III).

The most preferred ionic liquids according to the invention, may be described generally by formula (IV):

which is abbreviated herein as [BMIM][Y$^-$], where Y$^-$ represents any of the anions listed herein, with preference given to tetrafluoroborate [BF$_4^-$] and hexafluorophosphate [PF$_6^-$] in view of the excellent results obtained with these compounds. The ionic liquids of these two anions are thus designated 1-butyl-3-methylimidazolium tetrafluoroborate [BMIM][BF$_4^-$] and 1-butyl-3-methylimidazolium hexafluorophosphate [BMIM][PF$_6^-$], respectively.

Exemplary ionic liquids according to formula (IV) include, without limitation:
1-butyl-3-methylimidazolium tetrachloroaluminate;
1-butyl-3-methylimidazolium hexafluroantimonate;
1-butyl-3-methylimidazolium dicyanamide;
1-butyl-3-methylimidazolium thiocyanate;
1-butyl-3-methylimidazolium nitrate;
1-butyl-3-methylimidazolium chloride;
1-butyl-3-methylimidazolium iodide;
1-butyl-3-methylimidazolium trifluoroacetate;
1-butyl-3-methylimidazolium tetrafluoroborate;
1-butyl-3-methylimidazolium hexafluorophosphate;
1-butyl-3-methylimidazolium methylsulfonate;
1-butyl-3-methylimidazolium trifluoromethylsulfonate;
1-butyl-3-methylimidazolium tris(pentafluoroethyl)trifluorophosphate;
1-butyl-3-methylimidazolium bis(trifluoromethylsulfonyl)imide.

Other non-limiting examples of ionic liquids contemplated to be useful in the practice of the synthetic methods described herein are those wherein the butyl group of the foregoing ionic liquids is replaced with other C$_{1-10}$ alkyl chains, such as methyl, ethyl, propyl, pentyl, hexyl, heptyl, octyl, nonyl, or decyl. Additional non-limiting examples of ionic liquids are those other than formula (IV) ionic liquids, such as:
tri(ethyl)hexylammonium tetrafluoroborate;
tri(ethyl)hexylammonium hexafluorophosphate;
tri(ethyl)hexylammonium hexafluoroantimonate;
tri(ethyl)hexylammonium bis(trifluoromethylsulfonyl)imide;
tri(hexyl)tetradecylphosphonium tetrafluoroborate;
tri(hexyl)tetradecylphosphonium hexafluorophosphate;
tri(hexyl)tetradecylphosphonium hexafluoroantimonate;
tri(hexyl)tetradecylphosphonium bis(trifluoromethylsulfonyl)imide;
1-butyl-1-methylpyrrolidinium tetrachloroaluminate;
1-butyl-1-methylpyrrolidinium hexafluoroantimonate;
1-butyl-1-methylpyrrolidinium tetrafluoroborate;
1-butyl-1-methylpyrrolidinium hexafluorophosphate;
1-butyl-1-methylpyrrolidinium methylsulfonate;
1-butyl-1-methylpyrrolidinium trifluoromethylsulfonate;
1-butyl-1-methylpyrrolidinium tris(pentafluoroethyl)trifluorophosphate;
1-butyl-1-methylpyrrolidinium bis(trifluoromethylsulfonyl)imide;
N-butylpyridinium tetrachloroaluminate;
N-butylpyridinium hexafluoroantimonate;
N-butylpyridinium tetrafluoroborate;
N-butylpyridinium dicyanamide;
N-butylpyridinium thiocyante;
N-butylpyridinium nitrate;
N-butylpyridinium chloride;
N-butylpyridinium idoide;
N-butylpyridinium hexafluorophosphate;
N-butylpyridinium trifluoroacetate;
N-butylpyridinium methylsulfonate;
N-butylpyridinium trifluoromethylsulfonate;
N-butylpyridinium tris(pentafluoroethyl)trifluorophosphate;
N-butylpyridinium bis(trifluoromethylsulfonyl)imide; and
ethyl dimethyl propyl ammonium bis(trifluoromethylsulfonyl)imide.
ethyl dimethyl propyl ammonium hexafluorophosphate;
ethyl dimethyl propyl ammonium tetrafluoroborate; and
ethyl dimethyl propyl ammonium hexafluoroantimonate.

Preferred ionic liquids for the N-alkylation reaction are 1-butyl-3-methylimidazolium tetrafluoroborate [BMIM][BF$_4$] or 1-butyl-3-methylimidazolium hexafluorophosphate [BMIM][PF$_6$].

The ionic liquids are preferably of high purity, by which is meant greater than 95% purity, more preferably greater than 97% purity, and more preferred still greater than 98% purity, and optimally will be greater than 99% pure. Reference to purity herein will be understood to mean the absence of unreacted starting materials and byproducts from the reactions typically employed to form the ionic liquids, but does not necessarily preclude the presence of co-solvents, for example acetonitrile, to modify the viscosity and ionic conductivity of the solvent system, although in practice the use of co-solvents is not preferred.

The reaction temperature useful for achieving the N-alkylation reaction of acridan compounds 2 will typically be between about 150° C. and about 200° C., preferably in the range of about 160° C. to about 165° C. Heating can be accomplished thermally such as in an oil-bath or by microwave heating. The reaction times most useful to achieve good chemical conversion (i.e., >50%) may span the range of about 3 to about 24 hours although about 3 to about 5 hours is preferable.

In certain embodiments, the reaction may provide a chemical conversion greater than 50%. Preferably, the reaction provides a chemical conversion ≥60%. In certain exemplary embodiments, the reaction provides a chemical conversion from 60% to 70%.

After N-alkylation of the acridan compound 2, the N-alkyl acridan compound 3 may be oxidized using any suitable agent to obtain an N-alkyl acridinium compounds 4 by oxidation. Preferably, the N-alkyl acridan compound 3 is oxidize in the presence of gaseous oxygen. Typically, the oxidation step is performed in the presence of pure oxygen or air.

It is preferred to include a base in the ionic liquid reaction mixture, said base being unreactive with the alkylating agent under the reaction conditions described above. The base may be an inorganic or an organic base. The inorganic base is preferably a salt of carbonic acid, and more preferably the inorganic base is selected from the group consisting of potassium carbonate, sodium carbonate, or cesium carbonate. The organic base is preferably a pyridine derivative, and more preferably a sterically hindered pyridine derivative which will not react with the alkylating reagent. The preferred organic bases are 2,6-di-t-butylpyridine (DtBP) or 2,6-di-t-butyl-4-methylpyridine (DtMP), or a combination thereof. In some embodiments, the molar ratio of base to alkylating reagent is 1:2, although other ratios are also likely to be useful.

The inventive two-step reaction disclosed herein is extremely versatile. There is essentially no limitation on the structure of the acridine compounds which can be N-alkylated according to the invention, with the possible exception that strongly nucleophilic functional groups which may react with the alkylating agent should be avoided or should be protected with a suitable protecting group prior the carrying out the N-alkylation reaction.

In one embodiment, the starting acridine compounds used in the present invention are acridine esters having the following structure:

(Va)

where $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms; and $R_9$ is a substituted or unsubstituted alkyl or aryl moiety, typically a substituted aryl moiety having functional groups for forming conjugates with analytes, analyte analogs, or antibodies for such analytes. In some embodiments, R is a $C_{1-6}$ alkyl, alkenyl, alkynyl, aryl, or aralkyl group, optionally containing 1 to 6 heteroatoms selected from the group consisting of oxygen, nitrogen and sulfur. In one embodiment, $R_7$ and $R_8$ each represent hydrogen. In another embodiment, $R_7$ and $R_8$ are substituents on the C2 and C7 carbon atoms of the acridine nucleus, respectively. In a particularly interesting variant of the case where $R_7$ and $R_8$ are of the form —OR, R may comprise one or more ethylene glycol units of the form —(O—CH$_2$—CH$_2$)$_n$— (n=1-5) or may comprise sulfopropyl groups (—CH$_2$—CH$_2$—CH$_2$—SO$_3^-$), or combinations thereof, such as for example —(O—CH$_2$—CH$_2$)$_n$—CH$_2$—CH$_2$—CH$_2$—SO$_3^-$ or —CH$_2$—CH$_2$—CH$_2$—SO$_2$—NH—(O—CH$_2$—CH$_2$)$_n$—, or the like, and R may optionally be a branched substituent.

Preferred structures of the acridine esters according to this embodiment will have the structure:

(Vb)

where $R_7$ and $R_8$ are as defined above, $R_{10}$ and $R_{11}$ can be the same or different and represent hydrogen, an alkyl, alkenyl, alkynyl, aryl, or aralkyl group containing up to 20 heteroatoms, and $R_{12}$ is —OR (where R is defined as above).

Preferably, $R_{12}$ is —OR, where R is methyl, ethyl, propyl, or isopropyl.

Other preferred structures of the acridine ester compounds have the form:

(Vc)

where $R_{12}$ is as defined above.

Preferably, $R_{12}$ is —OR and R is selected from the group consisting of methyl, ethyl or isopropyl substituents.

The starting acridines may be reacted to with a reducing agent to convert the acridine compound having the structure of formula (Vb) to an acridan compound having the structure of formula (Vd):

(Vd)

wherein $R_7$, $R_8$, $R_{10}$, $R_{11}$ and $R_{12}$ are as defined above;

The acridan compound having the structure of formula (Vd) may be reacted with an alkylating agent in an ionic liquid solvent to thereby convert the acridan compound to an N-alkylacridan having the structure of formula (Ve):

(Ve)

wherein $R_7$, $R_8$, $R_{10}$, $R_{11}$ and $R_{12}$ are as defined above.

Further, the N-alkylacridan having the structure of formula (Ve) may be oxidized to thereby convert said N-alkylacridan to an acridinium ester having the structure of formula (V):

(V)

wherein $R_7$, $R_8$, $R_{10}$, $R_{11}$ and $R_{12}$ are as defined above.

In another embodiment, acridine sulfonamide compounds may be used as the starting acridine compound in the transformation to acridinium sulfonamides. Typically, the acridine sulfonamides will have the following structure:

(VIa)

where $R_7$ and $R_8$ are independently selected and are as defined above, and $R_{13}$ and $R_{14}$ can be the same or different and represent an alkyl, alkenyl, alkynyl, aryl, or aralkyl group containing up to 20 heteroatoms.

The starting acridines may be reacted to with a reducing agent to convert the acridine compound having the structure of formula (VIa) to an acridan compound having the structure of formula (VIb):

(VIb)

wherein $R_7$, $R_8$, $R_{13}$ and $R_{14}$ are as defined above;

The acridan compound having the structure of formula (VIb) may be reacted with an alkylating agent in an ionic liquid solvent to thereby convert the acridan compound to an N-alkylacridan having the structure of formula (VIc):

(VIc)

wherein $R_7$, $R_8$, $R_{13}$ and $R_{14}$ are as defined above.

Further, the N-alkylacridan having the structure of formula (VIc) may be oxidized to thereby convert said N-alkylacridan to an acridinium ester having the structure of formula (VI):

(VI)

Further examples of compounds which can be prepared according to the methods of the invention include all acridinium esters and acridinium sulfonamides disclosed in U.S. Patent Pub. 2005/0221390 and U.S. Patent Pub. 2004/0063147, the disclosures of which are hereby incorporated by reference herein.

Example I

N-Alkylation of Acridine Esters with Sodium 3-Bromopropanesulfonate in Ionic Liquids

The procedure for N-alkylation of an acridine dimethylphenyl ester 5 directly to an N-sulfopropyl acridinium dimethylphenyl ester 6 in ionic liquids following the general synthetic methods described by Natrajan and Wen, in *Green Chem.*, 2011, 13, 913-921 and U.S. Patent Application Publication No. 2010/0256380 was investigated. The process of directly N-alkylating acridine dimethylphenyl ester 5, in an ionic liquid with sodium 3-bromopropane sulfonate is illustrated as follows:

5
R = methyl, 5a
R = benzyl, 5d

+

6
R = methyl, 6a
R = benzyl, 6d

A number of different exemplary reactions, Examples 1 through 10 were conducted to determine the extent of conversion of the acridine dimethylphenyl esters 5, directly to the N-sulfopropyl acridinium dimethylphenyl esters 6 in ionic liquids. Each reaction mixture comprises 0.065 M acridine dimethylphenyl esters 5, where R is either methyl 5a or benzyl 5d, in an ionic liquid, which may be 1-butyl-3-methylimidazolium tetrafluoroborate [BMIM][BF$_4$], 1-butyl-3-methylimidazolium hexafluorophosphate [BMIM][PF$_6$], or tetraethylammonium triflate [TEA][OTf], as specified below in Table 2. The reaction mixture also includes two equivalents (as compared to the amount of acridine ester) of a base, as specified in Table 2. In certain examples described in Table 2 where a base is not specified, the base is absent from the reaction mixture. The reaction mixture further comprises sodium 3-bromopropanesulfonate as the non-toxic alkylating agent. The amount of alkylating agent is specified in Table 2 in equivalents of the amount of acridine ester present in the reaction mixture.

TABLE 2

| Example | Acridine ester | Ionic liquid | Base | Sodium 3-Bromopropanesulfonate (equivalents) |
|---|---|---|---|---|
| 1 | Acridine methyl ester, 5a | [BMIM][BF$_4$] | — | 10 |
| 2 | Acridine methyl ester, 5a | [BMIM][BF$_4$] | 2,6-di-t-butylpyridine | 10 |
| 3 | Acridine methyl ester, 5a | [BMIM][BF$_4$] | Potassium carbonate | 10 |
| 4 | Acridine methyl ester, 5a | [BMIM][BF$_4$] | Potassium carbonate | 20 |
| 5 | Acridine methyl ester, 5a | [BMIM][PF$_6$] | — | 10 |
| 6 | Acridine methyl ester, 5a | [TEA][OTf] | — | 10 |
| 7 | Acridine methyl ester, 5a | [TEA][OTf] | Potassium carbonate | 10 |
| 8 | Acridine benzyl ester, 5d | [BMIM][BF$_4$] | — | 10 |
| 9 | Acridine benzyl ester, 5d | [BMIM][BF$_4$] | 2,6-di-t-butylpyridine | 10 |
| 10 | Acridine benzyl ester, 5d | [BMIM][BF$_4$] | Potassium carbonate | 10 |

Each of the reaction mixtures of Examples 1 through 10 were heated at 160-165° C. under a nitrogen atmosphere for 3 hours. The percentage of conversation for each of the exemplary reactions was measured by HPLC analysis based on the amount of acridinium dimethylphenyl ester 6 produced compared to the amount of acridine dimethylphenyl ester 5 remaining in the reaction mixture. The data for each of these exemplary reactions is provided below in Table 3.

TABLE 3

| Example | % Conversion |
|---|---|
| 1 | 14 |
| 2 | 16 |
| 3 | 13 |
| 4 | 16 |
| 5 | <10 |
| 6 | <10 |
| 7 | <10 |
| 8 | 16 |
| 9 | <10 |
| 10 | <10 |

As shown in Table 3, directly N-alkylating an acridine dimethylphenyl ester 5 with sodium 3-bromopropane sulfonate to produce an N-sulfopropyl acridinium dimethylphenyl ester 6 in an ionic liquid resulted in poor conversation. As can be seen from Examples 1 through 10, the percentage conversion for all of these examples are below 20%. This poor conversion is attributable to a combination of poor reactivity of the acridine nitrogen as well as to attenuated reactivity of the alkylating reagent sodium 3-bromopropane sulfonate.

Example II

N-Alkylation of Acridan Dimethylphenyl Esters with Sodium 3-Bromopropanesulfonate in Ionic Liquids The extent of conversion for N-alkylation of an acridan dimethylphenyl ester 7 to an N-sulfopropyl acridinium dimethylphenyl ester 6 in ionic liquids according to the inventive process of the present invention was also investigated. The process of directly N-alkylating an acridan dimethylphenyl ester 7, in an ionic liquid is illustrated as follows:

7
R = methyl, 7a
R = ethyl, 7b
R = isopropyl, 7c

6
R = methyl, 6a
R = ethyl, 6b
R = isopropyl, 6c

A number of different exemplary reactions, Examples 11 through 19 were conducted to determine the extent of conversion of the acridan dimethylphenyl ester 7, to the N-sulfopropyl acridinium dimethylphenyl ester 6 by N-alkylation of the acridan dimethylphenyl ester 7 in ionic liquids and oxidizing the resulting product to produce the N-sulfopropyl acridinium dimethylphenyl ester 6. Each reaction mixture of Examples 11 through 15 and 17 through 19 comprises 0.129 M acridan dimethylphenyl ester 7, where R is either methyl 7a, ethyl 7b, or isopropyl 7c, in the ionic liquid 1-butyl-3-methylimidazolium tetrafluoroborate [BMIM][BF$_4$], as specified below in Table 3. Example 16 shown below in Table 3 comprises 0.065M acridan dimethylphenyl ester 7, where R methyl 7a, in the ionic liquid 1-butyl-3-methylimidazolium tetrafluoroborate [BMIM][BF$_4$]. Example 20 shown in Table 3 was conducted in sulfolane, in the absence of an ionic liquid. The reaction mixture of Example 20 comprises 0.129 M acridan dimethylphenyl ester 7, where R is isopropyl 7c.

The reactions may also include a base, as specified in Table 4. In Example 11 where a base is not specified, the base is absent from the reaction mixture. In Examples 12 and 14-20 the reaction mixture also includes two equivalents (as compared to the amount of acridan ester) of a base, as specified in Table 4. In Example 13, the reaction mixture includes four equivalents of the base 2,6-di-t-butylpyridine. The reaction mixture further comprises sodium 3-bromopropane sulfonate as the alkylating agent. The amount of alkylating agent is specified in Table 4 in equivalents of the amount of acridan ester present in the reaction mixture.

TABLE 4

| Example | Acridan ester | Ionic liquid or solvent | Base | Sodium 3-Bromopropanesulfonate (equivalents) |
|---|---|---|---|---|
| 11 | Acridan methyl ester, 7a | [BMIM][BF$_4$] | — | 10 |
| 12 | Acridan methyl ester, 7a | [BMIM][BF$_4$] | 2,6-di-t-butylpyridine | 10 |
| 13 | Acridan methyl ester, 7a | [BMIM][BF$_4$] | 2,6-di-t-butylpyridine | 20 |

TABLE 4-continued

| Example | Acridan ester | Ionic liquid or solvent | Base | Sodium 3-Bromopropanesulfonate (equivalents) |
|---|---|---|---|---|
| 14 | Acridan methyl ester, 7a | [BMIM][BF$_4$] | Potassium carbonate | 10 |
| 15 | Acridan methyl ester, 7a | [BMIM][BF$_4$] | Potassium carbonate | 10 |
| 16 | Acridan methyl ester, 7a | [BMIM][BF$_4$] | Potassium carbonate | 20 |
| 17 | Acridan methyl ester, 7a | [BMIM][BF$_4$] | Potassium carbonate | 10 |
| 18 | Acridan ethyl ester, 7b | [BMIM][BF$_4$] | Potassium carbonate | 10 |
| 19 | Acridan isopropyl ester, 7c | [BMIM][BF$_4$] | Potassium carbonate | 10 |
| 20 | Acridan isopropyl ester, 7c | sulfolane | Potassium carbonate | 10 |

Each of the reaction mixtures of Examples 11 through 15, and 18 through 20 were heated at 160-165° C. under a nitrogen atmosphere for 3 hours, followed by air oxidation. Example 16 was at 160-165° C. under an argon atmosphere for 3 hours, followed by air oxidation. Example 17 was heated at 190° C. under a nitrogen atmosphere for 2 hours, followed by air oxidation. The reaction was then cooled to room temperature and dissolved in methanol (20 mL). HPLC analysis was performed using a Phenomenex C$_{18}$, 10 micron, 3.9×300 mm column and a 30 minute gradient of 10→100% MeCN/water (each with 0.05% trifluoroacetic acid) at a flow rate of 1.0 mL/minute and UV detection at 260 nm.

The percentage of conversion for each of the exemplary reactions was measured by HPLC analysis based on the amount of acridinium dimethylphenyl ester 6 produced compared to the amount of acridan dimethylphenyl ester 7 remaining in the reaction mixture. The data for each of these exemplary reactions is provided below in Table 5.

TABLE 5

| Example | % Conversion |
|---|---|
| 11 | 22 |
| 12 | 52 |
| 13 | 44 |
| 14 | 48 |
| 15 | 44 |
| 16 | 45 |
| 17 | 48 |
| 18 | 47 |
| 19 | 51 |
| 20 | <10 |

In contrast to the results of Example I, N-alkylation of the acridan dimethylphenyl ester 7 with 10-20 equivalents of sodium 3-bromopropane sulfonate in the ionic liquid [BMIM][BF$_4$] provided approximately ~50% conversion to the N-sulfopropyl acridinium dimethylphenyl ester 6 following air oxidation of the N-sulfopropylacridan intermediate (not shown). Both inorganic (potassium carbonate) and organic (di-tert-butylpyridine) bases were effective in these N-alkylation reactions. In the absence of base (Example 11), conversion of the acridan dimethylphenyl ester 7 to the N-sulfopropyl acridinium dimethylphenyl ester 6 was significantly lower.

Example 20 shows that the use of an ionic liquid in the N-alkylation step is critical to obtaining a high rate of conversion. The absence of an ionic liquid in Example 20, resulted in a poor conversion rate, below 10%, and produced a number of different undesired decomposition products.

Comparing the extent of conversation for the reactions of Examples I and II, it can be seen that the present invention, which requires a first step of reducing an acridine to an acridan takes advantage of the increased reactivity of acridans in ionic liquids towards sodium 3-bromopropane sulfonate and, eliminates use of the carcinogenic reagent 1,3-propane sultone. This novel process provides for an efficient and environmentally safer method of N-alkylation for the introduction of the hydrophilic N-sulfopropyl group in commercially useful, chemiluminescent acridinium ester labels.

Example III

Synthesis of 2'-6'-dimethyl-4'-methoxycarbonylphenyl acridan-9-carboxylate 7a

Figure 1:
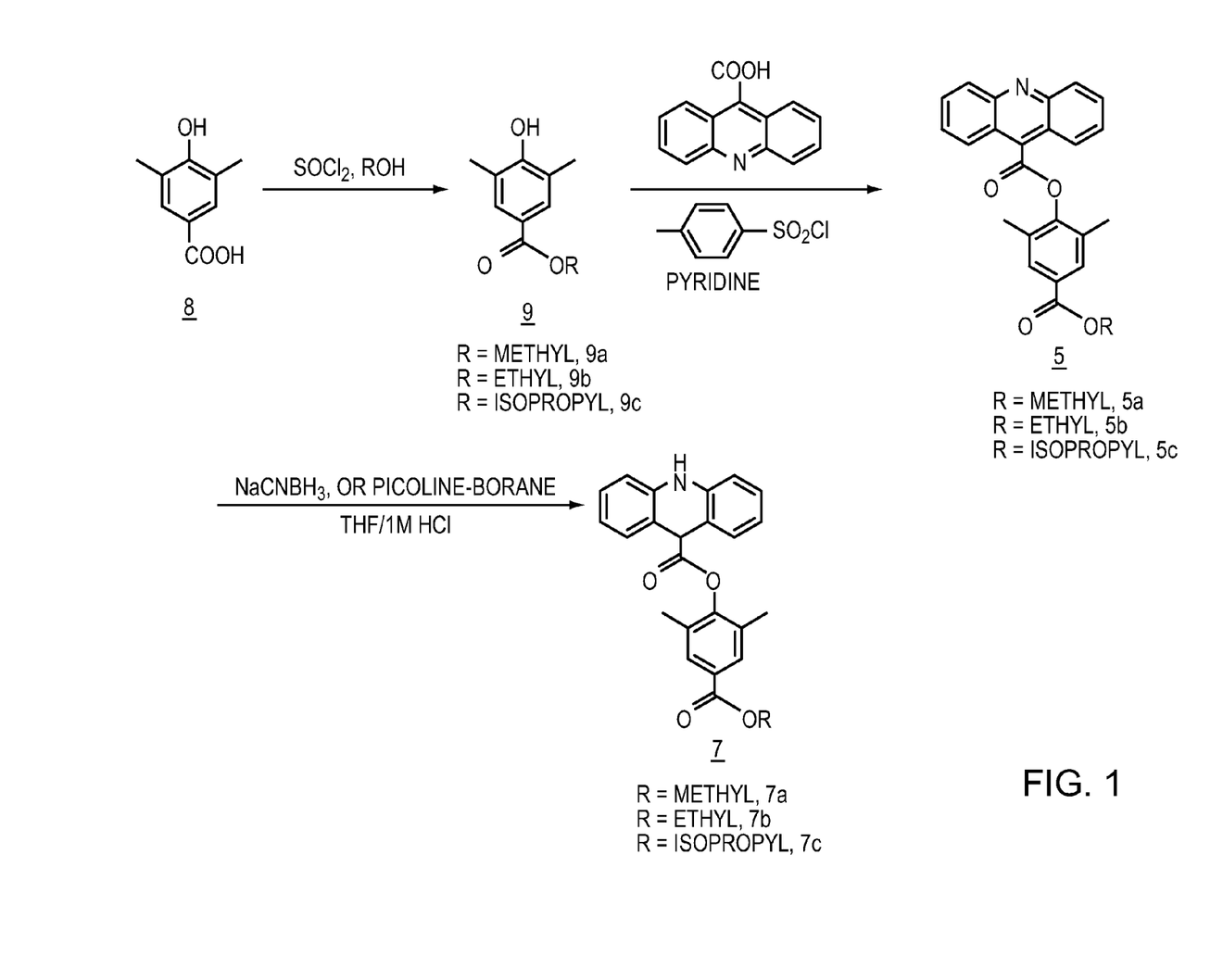
FIG. 1 illustrates the preparation of an acridan ester to increase the reactivity of the acridine nitrogen for N-alkylation with an alkylating reagent that is less reactive than 1,3-propane sultone.

FIG. 1 provides an exemplary synthesis of an acridan compound useful for the novel process for the present invention. The exemplary synthesis is described below with respect to producing 2'-6'-dimethyl-4'-methoxycarbonylphenyl acridan-9-carboxylate (7a), it is understood that this synthesis is equally applicable for the preparation of compounds having the structure of 7, where R can be an alkyl, alkenyl, alkynyl, aryl, or aralkyl group containing up to 20 heteroatoms.

a) Methyl-3,5-dimethyl-4-hydroxybenzoate, compound 9a

A solution of 3.5-dimethyl-4-hydroxybenzoic acid (5 g, 0.030 mole) in methanol (75 mL) was cooled in an ice-bath and thionyl chloride (8 mL) was added drop wise. The reaction was then warmed to room temperature and stirred for 16 hours. Solid sodium bicarbonate was then added to neutralize the acid and the resulting suspension was concentrated under reduced pressure. The residue was partitioned between water and ethyl acetate (75 mL each). The ethyl acetate layer was separated and dried over anhydrous magnesium sulfate. It was then concentrated under reduced pressure to afford a tan powder. Yield=5.49 g (quantitative).

Compounds 9b (ethyl-3,5-dimethyl-4-hydroxybenzoate, 97% yield) and 9c (isopropyl-3,5-dimethyl-4-hydroxybenzoate, 93% yield) were prepared similarly.

b) 2'-6'-Dimethyl-4'-methoxycarbonylphenyl acridine-9-carboxylate, compound 5a

A suspension of acridine-9-carboxylic acid (5 g, 0.0224 mole) in anhydrous pyridine (100 mL) was treated with p-toluenesulfonyl chloride (8.5 g, 0.0446 mole). The reaction was stirred under a nitrogen atmosphere for 15-20 minutes and then methyl 3,5-dimethyl-4-hydroxybenzoate (4 g, 0.0222 mole) was added. The reaction was stirred at room temperature under a nitrogen atmosphere for 16 hours and then concentrated under reduced pressure. The crude reaction mixture was dissolved in chloroform (150 mL) and washed with 5% sodium carbonate (400 mL), water (100 mL), 10% HCl (200 mL) and water (100 mL) in that order. The chloroform solution was then dried over anhydrous magnesium sulfate and concentrated under reduced pressure. The crude product (10.8 g) was purified by flash chromatography on silica using 70% hexanes, 25% chloroform, 5% ethyl acetate as eluent. Yield=5.9 g (68%); bright yellow powder.

Compounds 5b (quantitative yield) and 5c (91% yield) were prepared similarly.

c) 2'-6'-Dimethyl-4'-methoxycarbonylphenyl acridan-9-carboxylate, compound 7a: Reduction with sodium cyanoborohydride A solution of 2'-6'-dimethyl-4'-methoxycarbonylphenyl acridine-9-carboxylate (1 g, 0.0026 mole, 5a) in tetrahydrofuran (100 mL) was mixed with 1M HCl (40 mL). The resulting yellow solution was treated with sodium cyanoborohydride (0.82 g, 0.0130 mole) in one portion. The yellow color of the solution disappeared instantly. The reaction was stirred at room temperature. After 30 minutes, the reaction was quenched with acetone (10 mL) and stirred for 5 minutes. The reaction mixture was then concentrated under reduced pressure and the residue was partitioned between water (30 mL) and chloroform (50-60 mL). The chloroform layer was separated and washed with aqueous sodium bicarbonate. It was then dried over anhydrous magnesium sulfate and concentrated under reduced pressure. TLC analysis (silica, 25% ethyl acetate, 75% hexanes) indicated clean product with no trace of starting material. Yield of compound 7a=0.95 g (95%, white powdery solid).

Compounds 7b (quantitative yield) and 7c (quantitative yield) were prepared in a similar manner.

d) 2'-6'-Dimethyl-4'-ethoxycarbonylphenyl acridan-9-carboxylate, compound 7b: Reduction with picoline-borane A solution of 2'-6'-dimethyl-4'-ethoxycarbonylphenyl acridine-9-carboxylate (0.84 g, 0.0021 mole, 5b) in tetrahydrofuran (40 mL) was mixed with 1M HCl (4 mL). The resulting yellow solution was treated with picoline-borane (0.27 g, 0.0025 mole) in one portion. The reaction was stirred at room temperature. After 2 hours, the reaction was quenched with 10% HCl (10 mL) and stirred for 3 hours. The reaction mixture was then concentrated under reduced pressure to 10-15 mL and was extracted with ethyl acetate (70 mL). The ethyl acetate layer was separated and washed twice with water (2×25 mL) followed by aqueous sodium bicarbonate (25 mL) and brine (25 mL). It was then dried over anhydrous sodium sulfate and concentrated under reduced pressure. TLC analysis (silica, 25% ethyl acetate, 75% hexanes) indicated clean product with no trace of starting material. Yield of compound 7b=0.84 g (quantitative, light yellow powdery solid).

Compounds 7c (quantitative yield) was prepared in a similar manner.

Example IV

General Procedure for N-Alkylation of Acridine Dimethylphenyl Esters 5 with Sodium 3-Bromopropane Sulfonate in Ionic Liquids A mixture of 2'-6'-dimethyl-4'-methoxycarbonylphenyl acridine-9-carboxylate 5a (25 mg, 0.065 mmole), sodium 3-bromopropane sulfonate (0.146 g, 0.65 mmole) and potassium carbonate (18 mg, 0.13 mmole) in [BMIM][BF$_4$] (1 mL) was heated at 160-165° C. under a nitrogen atmosphere for 3 hours. The reaction was then cooled to room temperature and dissolved in methanol (20 mL). HPLC analysis was performed using a Phenomenex C$_{18}$, 10 micron, 3.9×300 mm column and a 30 minute gradient of 10→100% MeCN/water (each with 0.05% trifluoroacetic acid) at a flow rate of 1.0 mL/minute and UV detection at 260 nm. Poor conversion to the product 2'-6'-dimethyl-4'-methoxycarbonylphenyl 10-sulfopropylacridinium-9-carboxylate 6a (~13%) eluting at 17 minutes was observed. Starting material was observed to elute at 24 minutes.

Example V

General Procedure for the N-Alkylation of Acridan Dimethylphenyl Esters 7 with Sodium 3-Bromopropane Sulfonate in Ionic Liquids A mixture of 2'-6'-dimethyl-4'-methoxycarbonylphenyl acridan-9-carboxylate 7a (25 mg, 0.065 mmole), sodium 3-bromopropane sulfonate (0.146 g, 0.65 mmole) and potassium carbonate (18 mg, 0.13 mmole) in [BMIM][BF$_4$] (1 mL) was heated at 160-165° C. under a nitrogen atmosphere for 3 hours then open to air for one hour. The reaction was then cooled to room temperature and dissolved in methanol (20 mL). HPLC analysis was performed using a Phenomenex C$_{18}$, 10 micron, 3.9×300 mm column and a 30 minute gradient of 10→100% MeCN/water (each with 0.05% trifluoroacetic acid) at a flow rate of 1.0 mL/minute and UV detection at 260 nm. 48% conversion to the product 2'-6'-dimethyl-4'-methoxycarbonylphenyl 10-sulfopropylacridinium-9-carboxylate 6a eluting at 17 minutes was observed. Oxidized starting material 5a was observed to elute at 24 minutes.

Example VI

Figure 2:
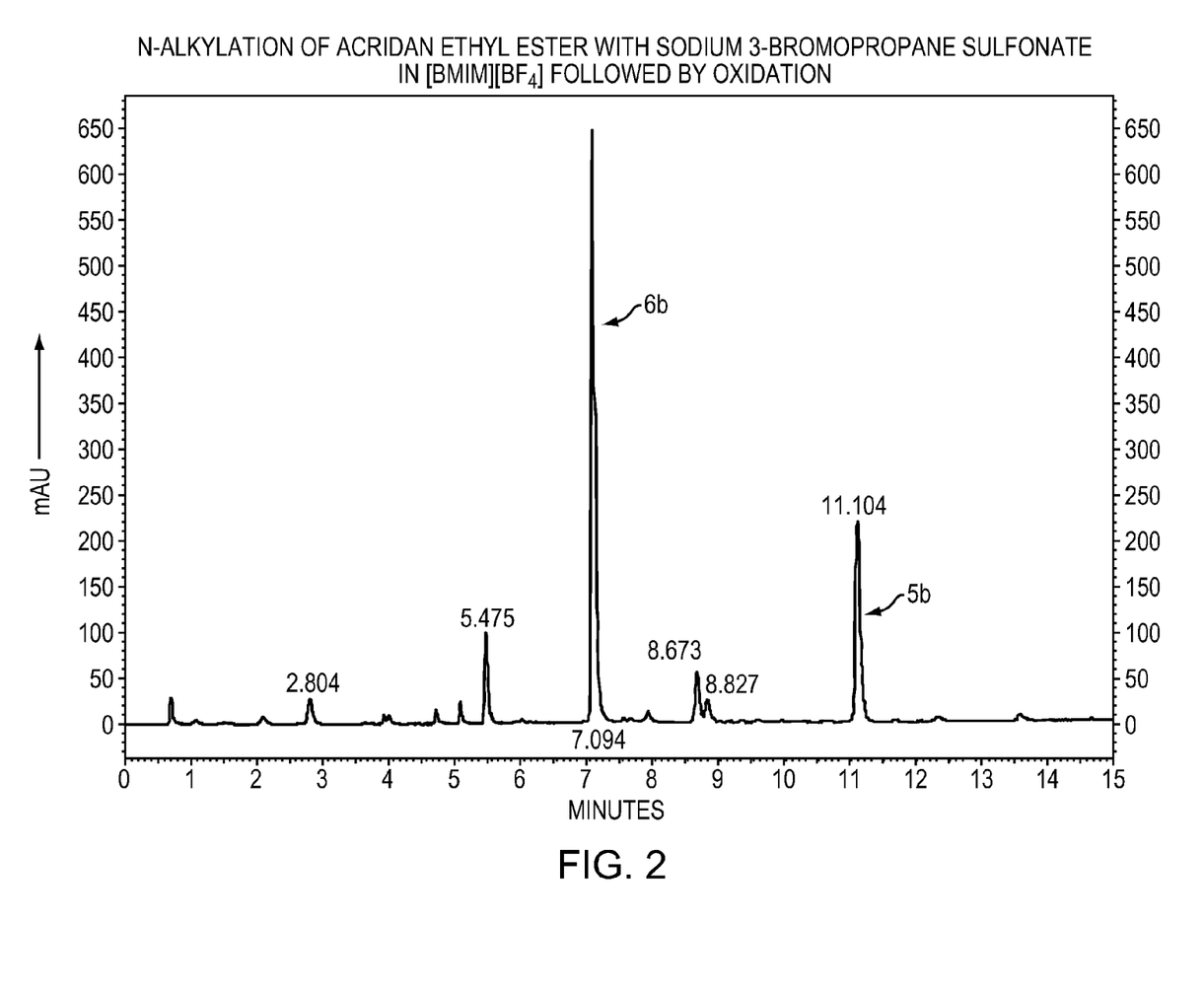
FIG. 2 is an HPLC analysis of N-alkylation of 2'-6'-dimethyl-4'-ethoxycarbonylphenyl acridan-9-carboxylate with sodium 3-bromopropane sulfonate in ionic liquid followed by oxidation showing a major peak corresponding to the corresponding acridinium ester, 2'-6'-dimethyl-4'-ethoxycarbonylphenyl 10-sulfopropylacridinium-9-carboxylate, and a minor peak for the oxidized acridan precursor material.
Figure 3:
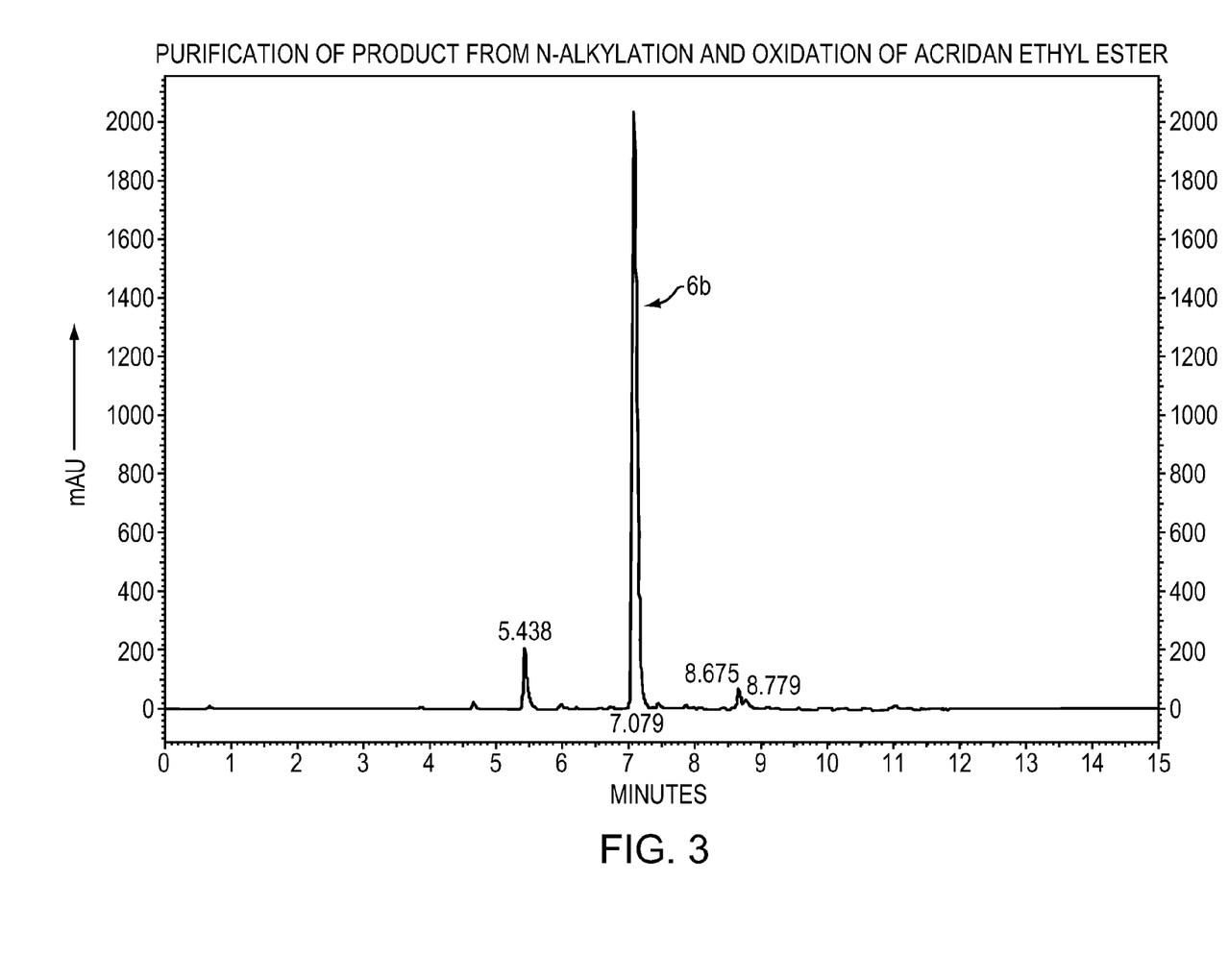
FIG. 3 is an HPLC analysis of the reaction product of FIG. 2 after purification by silica chromotagraphy.

N-Alkylation on a Gram Scale of Acridan Dimethylphenyl Esters with Sodium 3-Bromopropane Sulfonate in Ionic Liquids A mixture of 2'-6'-dimethyl-4'-ethoxycarbonylphenyl acridan-9-carboxylate 7b (1 g, 2.491 mmoles), sodium 3-bromopropane sulfonate (2.8 g, 12.45 mmoles) and potassium carbonate (0.689 g, 4.98 mmoles) in [BMIM][BF$_4$] (10 mL) was heated at 165° C. under an argon atmosphere for 5 hours. It was then heated open to air for an additional 3 hours. The reaction was then cooled to room temperature and a small portion was dissolved in methanol and analyzed by HPLC using a 4.0×50 mm, YMC, 3 micron C$_{18}$ column and 10-minute gradient of 10→90% MeCN/water (each with 0.05% TFA) at a flow rate of 1 mL/minute and UV detection at 260 nm. Product 6b eluted at 7.1 minutes (69% conversion) and oxidized starting material 5b eluted at 11.3 minutes (FIG. 2). Water (100 mL) was added to the reaction mixture which was then extracted with ethyl acetate (4×100 mL). The ethyl acetate solution was concentrated under reduced pressure to give a brown oil which was purified by flash chromatography on silica gel using ethyl acetate to elute unreacted starting material followed by 40% methanol, 60% ethyl acetate to elute product. The product was recovered as a viscous oil. Yield=0.91 g (62% yield, 89% purity by HPLC analysis, FIG. 3). Yield of oxidized starting material 5b=0.24 g (24%).

A similar reaction on a 1 g scale afforded 71% conversion. Yield of product=0.87 g (67% yield, 90% purity by HPLC analysis). Yield of oxidized starting material 5b=0.31 g (31%). (Oxidized starting material is recovered in the 25-30% range that can potentially be recycled for the reduction reaction.

The patents, patent documents, and publications cited herein are incorporated by reference in their entirety, as if each were individually incorporated by reference. Various

We claim:

1. A method for N-alkylation of an acridine compound, the method comprising:
   (a) reacting said acridine compound with a reducing agent to thereby convert said acridine compound to an acridan compound;
   (b) reacting said acridan compound with an alkylating agent in an ionic liquid solvent to thereby convert said acridan compound to an N-alkylacridan; and
   (c) oxidizing said N-alkylacridan to thereby convert said N-alkylacridan to an N-alkyl acridinium compound.

2. The method according to claim 1, wherein said alkylating agent is a sulfonate.

3. The method according to claim 2, wherein said sulfonate has the structure:

$$L'\!-\!(CH_2)_n\!-\!\overset{O}{\underset{O}{\overset{\|}{\underset{\|}{S}}}}\!-\!O^\ominus\ A^\oplus$$

where n is an integer from 1 to 20,
L is a halogen or —OR$^L$, wherein R$^L$ is an acetyl or a sulfonyl group, optionally substituted with one or more linear, branched or cyclic alkyl groups, wherein said alkyl groups optionally comprise one or more heteroatoms and optionally include one or more unsaturated bonds, and
A is a counterion.

4. The method according to claim 3, wherein n is an integer from 1 to 10.

5. The method according to claim 4, wherein n is an integer from 1 to 5.

6. The method according to claim 3, wherein L' is chloride, bromide, or —OR$^L$, where R$^L$ is selected from the group consisting of acetyl, methanesulfonyl, or p-toluenesulfonyl groups.

7. The method according to claim 3, wherein A is a sodium or potassium cation.

8. The method according to claim 2, wherein said alkylating agent is sodium 3-bromopropanesulfonate.

9. The method according to claim 1, wherein said reducing agent is a metal hydride.

10. The method according to claim 1, wherein said reducing agent is a borane complex of an amine or a cyanoborohydride complex comprising an alkali metal cation.

11. The method according to claim 10, wherein said reducing agent is selected from the group consisting of sodium borohydride, lithium borohydride, potassium borohydride, sodium cyanoborohydride, potassium cyanoborohydride, or picoline-borane.

12. The method according to claim 11, wherein said reducing agent is sodium cyanoborohydride or picoline-borane.

13. The method according to claim 1, wherein said reducing agent is a catalyst for catalytic hydrogenation.

14. The method according to claim 13, wherein said reducing agent comprises platinum or palladium.

15. The method according to claim 1, wherein said ionic liquid solvent is of the form:

$$\left[H_3C\!-\!\underset{+}{N}\!\!\diagup\!\!\diagdown\!\!N\!-\!(CH_2)_n CH_3\right][Y^-]$$

where n is an integer from one to nine; and Y is selected from the group consisting of tetrachloroaluminate; hexafluroantimonate; dicyanamide; thiocyanate; nitrate; chloride; iodide; trifluoroacetate; tetrafluoroborate; hexafluorophosphate; methylsulfonate; trifluoromethylsulfonate; tris(pentafluoroethyl)trifluorophosphate; bis(trifluoroinethylsulfonyl)imide, and combinations thereof.

16. The method according to claim 15, wherein the ionic solvent comprises [BMIM][PF$_6$] (1-butyl-3-methylimidazolium hexafluorophosphate).

17. The method according to claim 15, wherein the ionic solvent comprises [BMIM][BF$_4$] (1-butyl-3-methylimidazolium tetrafluoroborate).

18. The method according to claim 1, wherein step (b) is reacted in the presence of a base, wherein said base is unreactive with said alkylating agent under the reaction conditions.

19. The method according to claim 18, wherein said base is selected from the group consisting of potassium carbonate, sodium carbonate, and cesium carbonate.

20. The method according to claim 18, wherein said base is a sterically hindered pyridine derivative.

21. The method according to claim 20, wherein said base comprises 2,6-di-t-butylpyridine (DtBP) or 2,6-di-t-butyl-4-methylpyridine (DtBMP), or a combination thereof.

22. The method according to claim 1, wherein said acridine compound is an acridine ester.

23. The method according to claim 1, wherein said acridine compound is an acridine sulfonamide.

24. A method for preparing an acridinium ester compound having the structure of formula (V):

(V)

[structure of acridinium ester with substituents R$_7$, R$_8$, R$_{10}$, R$_{11}$, R$_{12}$ and propyl sulfonate group on N]

wherein R$_7$ and R$_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; wherein R$_{10}$ and R$_{11}$ can be the same or different and represent hydrogen, an alkyl, alkenyl, alkynyl, aryl, or aralkyl group containing up to 20 heteroatoms; and wherein R.sub.12 is —OR; the method comprising: (a) reacting an acridine compound having the structure of formula (Vb)

(Vb)

wherein $R_7$, $R_8$, $R_{10}$, $R_{11}$ and $R_{12}$ are as defined above, with a reducing agent to thereby convert said acridine compound to an acridan compound having the structure of formula (Vd):

(Vd)

wherein $R_7$, $R_8$, $R_{10}$, $R_{11}$ and $R_{12}$ are as defined above; (b) reacting said acridan compound with an alkylating agent in an ionic liquid solvent to thereby convert said acridan compound to an N-alkylacridan having the structure of formula (Ve):

(Ve)

wherein $R_7$, $R_8$, $R_{10}$, $R_{11}$ and $R_{12}$ are as defined above; and (c) oxidizing said N-alkylacridan to thereby convert said N-alkylacridan to said acridinium ester.

25. A method for preparing an acridinium sulfonamide compound having the structure of formula (VI):

(VI)

wherein $R_7$ and $R_8$ can be the same or different, and are selected from the group consisting of hydrogen, halogen, —OR, and R; where ft is an alkyl, alkenyl, alkynyl, aryl, or aralkyl group containing up to 20 heteroatoms selected from oxygen, sulfur, and nitrogen; and wherein $R_{13}$ and $R_{14}$ can be the same or different and represent an alkyl, alkenyl, alkynyl, aryl, or aralkyl group containing up to 20 heteroatoms; the method comprising: (a) reacting an acridine compound having the structure of formula (VIa)

(VIa)

wherein $R_7$, $R_8$, $R_{13}$ and $R_{14}$ are as defined above, with a reducing agent to thereby convert said acridine compound to an acridan compound having the structure of formula (VIb):

(VIb)

wherein $R_7$, $R_8$, $R_{13}$ and $R_{14}$ are as defined above; (b) reacting said acridan compound with an alkylating agent in an ionic liquid solvent to thereby convert said acridan compound to an N-alkylacridan having the structure of formula (VIc):

(VIc)

wherein $R_7$, $R_8$, $R_{13}$ and $R_{14}$ are as defined above; and (c) oxidizing said N-alkylacridan to thereby convert said N-alkylacridan to said acridinium ester.

26. A method for N-alkylation of an acridine compound, wherein said acridine compound contains an ester or sulfonamide functional group at the C-9 position of the acridine nucleus, the method comprising:

(a) reacting said acridine compound with a reducing agent to thereby convert said acridine compound to an acridan compound; wherein said reducing agent is selected from the group consisting of metal hydrides, boron hydrides, boron and nitrogen hydrides, borane-heterocyclic amine complexes, borane complexes comprising an alkali metal, cyanoborane complexes comprising an alkali metal, and metal catalysts for catalytic hydrogenation;

(b) reacting said acridan compound with an alkylating agent n an ionic liquid solvent to thereby convert said acridan compound to an N-alkylacridan; and (c) oxidizing said N-alkylacridan to thereby convert said N-alkylacridan to an N-alkyl acridinium compound.

27. The method according to claim 26, wherein said reducing agent is selected from the group consisting of sodium borohydride, lithium borohydride, potassium borohydride, sodium cyanoborohydride, potassium cyanoborohydride, picoline-borane, platinum, palladium, rhodium and ruthenium.

* * * * *